(12) United States Patent
Zhuang et al.

(10) Patent No.: US 12,398,199 B2
(45) Date of Patent: Aug. 26, 2025

(54) NANO ANTIBODY FOR NEUTRALIZING TOXICITY OF SARS-CoV-2 AND PREPARATION METHOD AND APPLICATION THEREOF

(71) Applicant: SYSVAX INC., Zhongshan (CN)

(72) Inventors: Wenchao Zhuang, Zhongshan (CN); Fusheng Li, Zhongshan (CN); Qianhui Li, Zhongshan (CN); Zhi Ling, Zhongshan (CN); Yunxing Zhao, Zhongshan (CN)

(73) Assignee: SYSVAX INC, Guangdong (CN)

( * ) Notice: Subject to any disclaimer, the term of this patent is extended or adjusted under 35 U.S.C. 154(b) by 1174 days.

(21) Appl. No.: 17/261,802

(22) PCT Filed: Jan. 7, 2021

(86) PCT No.: PCT/CN2020/132279
§ 371 (c)(1),
(2) Date: Jan. 20, 2021

(87) PCT Pub. No.: WO2022/048052
PCT Pub. Date: Mar. 10, 2022

(65) Prior Publication Data
US 2022/0372113 A1    Nov. 24, 2022

(30) Foreign Application Priority Data

Sep. 7, 2020   (CN) .......................... 202010926772.3

(51) Int. Cl.
*A61P 31/14*     (2006.01)
*A61K 39/00*    (2006.01)
*C07K 16/10*    (2006.01)

(52) U.S. Cl.
CPC .......... *C07K 16/1003* (2023.08); *A61P 31/14* (2018.01); *A61K 2039/505* (2013.01);
(Continued)

(58) Field of Classification Search
CPC .............. A61K 2039/505; A61P 31/14; C07K 16/1003; C07K 2317/22; C07K 2317/565;
(Continued)

(56) References Cited

FOREIGN PATENT DOCUMENTS

| CN | 111303279 A | 6/2020 |
|----|-------------|--------|
| CN | 112010967 A | 12/2020 |

OTHER PUBLICATIONS

Pardon E, et al. A general protocol for the generation of Nanobodies for structural biology. Nat Protoc. 2014;9(3):674-693 (Year: 2014).*
(Continued)

*Primary Examiner* — M Franco G Salvoza
*Assistant Examiner* — Marlene V Buckmaster
(74) *Attorney, Agent, or Firm* — D'Ambrosio & Menon, PLLC; Usha Menon

(57) ABSTRACT

The present disclosure discloses a nano antibody for neutralizing a toxicity of SARS-CoV-2 and preparation method thereof. The nano antibody comprises a complementarity determining region CDR comprising a CDR1, a CDR2 and a CDR3; an amino acid sequence of the CDR1 is selected from at least one of amino acid sequences shown in SEQ ID NO. 1 and SEQ ID NO. 2; an amino acid sequence of the CDR2 is selected from at least one of amino acid sequences shown in SEQ ID NO. 3, SEQ ID NO. 4, and SEQ ID NO. 5; and an amino acid sequence of the CDR3 is selected from at least one of amino acid sequences shown in any one of SEQ ID NO. 6 to SEQ ID NO. 9. The nano antibody for neutralizing the toxicity of SARS-CoV-2 has the advantages of a small molecular weight, a high affinity with the SARS-CoV-2, a low production cost, and the like.

7 Claims, 9 Drawing Sheets

Specification includes a Sequence Listing.

(52) U.S. Cl.
CPC .. *C07K 2317/565* (2013.01); *C07K 2317/567* (2013.01); *C07K 2317/76* (2013.01)

(58) Field of Classification Search
CPC ........ C07K 2317/567; C07K 2317/569; C07K 2317/76; C07K 2317/92
See application file for complete search history.

(56) References Cited

OTHER PUBLICATIONS

Jug, A et al. Biolayer interferometry and its applications in drug discovery and development. May 2024; TrAC Trends in Analytical Chemistry 176(7):117741. (Year: 2024).*

Wu Y, Li C, Xia S, et al. Identification of Human Single-Domain Antibodies against SARS-CoV-2. Cell Host Microbe. 2020;27(6):891-898.e5. (Year: 2020).*

Wrapp, D. etc. Structural Basis for Potent Neutralization of Betacoronaviruses by Single-Domain Camelid Antibodies Cell. May 28, 2020; vol. 181.

* cited by examiner

Purchase S1 protein to immunize a llama

↓

Collect a large amount of blood, and separate a peripheral blood mononuclear cell PBMC of the llama

↓

Extract mRNA, and reversely transcribe the mRNA into cDNA

↓

Design a primer voluntarily, and amplify a heavy chain variable region of an antibody through a two-step PCR

↓

Construct a phage display library of the heavy chain variable region of the antibody, a capacity of the immune library is $10^8$

↓

Directly construct an ELISA positive clone into an Escherichia coli expression vector for small expression

↓

Carry out a virus neutralization test on samples subjected to small expression to obtain a group of nano antibodies capable of neutralizing SARS-CoV-2

FIG. 1

SEQUENCE LISTING

```
<160> NUMBER OF SEQ ID NOS: 35

<210> SEQ ID NO 1
<211> LENGTH: 122
<212> TYPE: PRT
<213> ORGANISM: Artificial Sequence
<220> FEATURE:
<223> OTHER INFORMATION: synthesized

<400> SEQUENCE: 1

Gln Val Gln Leu Val Glu Ser Gly Gly Gly Leu Val Gln Ala Gly Asp
1               5                   10                  15

Ser Leu Arg Leu Ala Cys Ala Ala Thr Gly Arg Thr Leu Ser Asn Tyr
            20                  25                  30

Ile Met Gly Trp Phe Arg Gln Ala Pro Gly Lys Glu Pro Leu Phe Val
        35                  40                  45

Ala Ala Ile Ser Arg Ser Gly Val Ile Thr Lys Tyr Ala Asp Ser Val
    50                  55                  60

Glu Gly Arg Phe Thr Ile Ser Arg Asp Asn Ala Lys Asn Thr Ala Tyr
65                  70                  75                  80

Leu Gln Met Thr Ser Leu Glu Pro Glu Asp Thr Ala Val Tyr Tyr Cys
                85                  90                  95

Ala Ala Ser Ser Ser Lys Tyr Met Ala Thr Arg Glu Tyr Asp Tyr Trp
            100                 105                 110

Gly Gln Gly Thr Gln Val Thr Val Ser Ser
        115                 120

<210> SEQ ID NO 2
<211> LENGTH: 128
<212> TYPE: PRT
<213> ORGANISM: Artificial Sequence
<220> FEATURE:
<223> OTHER INFORMATION: synthesized

<400> SEQUENCE: 2

Gln Val Gln Leu Val Glu Ser Gly Gly Gly Leu Val Gln Pro Gly Ala
1               5                   10                  15

Ser Leu Arg Leu Ser Cys Ala Ala Ser Gly Arg Thr Phe Ser Ser Thr
            20                  25                  30

Gly Met Gly Trp Phe Arg Gln Ala Pro Gly Lys Glu Arg Glu Phe Val
        35                  40                  45

Ala Ala Ile Ser Gly Asp Gly Asp Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Trp Asp Thr Ala Val Tyr Tyr Cys
                85                  90                  95

Ala Ser Thr Arg Phe Thr Trp Gly Leu Tyr Ser Asp Phe Val Asn Ser
```

```
                100                 105                 110
Tyr Glu Tyr Asp Ala Trp Gly Gln Gly Thr Pro Val Thr Val Ser Ser
            115                 120                 125

<210> SEQ ID NO 3
<211> LENGTH: 128
<212> TYPE: PRT
<213> ORGANISM: Artificial Sequence
<220> FEATURE:
<223> OTHER INFORMATION: synthesized

<400> SEQUENCE: 3

Gln Val Gln Leu Val Glu Ser Gly Gly Leu Val Gln Pro Gly Gly
1               5                   10                  15

Ser Leu Arg Leu Ser Cys Ala Ala Ser Gly Arg Thr Phe Ser Ser Thr
            20                  25                  30

Gly Met Gly Trp Phe Arg Gln Gly Pro Gly Lys Glu Arg Glu Phe Val
            35                  40                  45

Ala Ala Ile Ser Gly Asp Gly Asp Thr Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Ala Arg Phe Thr Trp Gly Leu Tyr Ser Asp Phe Val Asn Ser
            100                 105                 110

Tyr Glu Tyr Asp Ala Trp Gly Gln Gly Thr Pro Val Thr Val Ser Ser
            115                 120                 125

<210> SEQ ID NO 4
<211> LENGTH: 128
<212> TYPE: PRT
<213> ORGANISM: Artificial Sequence
<220> FEATURE:
<223> OTHER INFORMATION: synthesized

<400> SEQUENCE: 4

Gln Val Gln Leu Val Glu Ser Gly Gly Leu Val Gln Pro Gly Ala
1               5                   10                  15

Ser Leu Arg Leu Phe Cys Val Ala Ser Gly Arg Thr Phe Ser Ser Thr
            20                  25                  30

Gly Met Gly Trp Phe Arg Gln Ala Pro Gly Lys Glu Arg Glu Phe Val
            35                  40                  45

Ala Ala Ile Ser Gly Pro Gly Asp Thr Thr Tyr Tyr Val Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Ala Gly Phe Thr Trp Gly Leu Tyr Ser Asp Phe Val Asn Ser
            100                 105                 110

Tyr Glu Tyr Asn Tyr Trp Gly Gln Gly Thr Pro Val Thr Val Ser Ser
            115                 120                 125

<210> SEQ ID NO 5
<211> LENGTH: 366
<212> TYPE: DNA
<213> ORGANISM: Artificial Sequence
<220> FEATURE:
```

<223> OTHER INFORMATION: synthesized

<400> SEQUENCE: 5

```
caggtgcagc tcgtggagtc tgggggagga ttggtgcagg ctggggactc tctgagactc    60
gcctgtgcag ccactggacg caccctcagt aactatatca tggctggtt ccgccaggct    120 ccaggaaagg aacctttgtt tgtagcagca attagccgga gtggtgtcat cacaaagtat    180
gcagactccg tagagggccg attcaccatc tccagagaca atgccaagaa cacggcgtat    240
ctgcagatga ctagtctgga acctgaagac acggccgtct attattgtgc agcatcgtct    300
agtaaataca tggctacgcg agagtatgac tactggggcc aggggaccca ggtcaccgtc    360
tcctca                                                                366
```

<210> SEQ ID NO 6
<211> LENGTH: 384
<212> TYPE: DNA
<213> ORGANISM: Artificial Sequence
<220> FEATURE:
<223> OTHER INFORMATION: synthesized

<400> SEQUENCE: 6

```
caggtgcagc tggtggagtc tgggggagga ttggtgcagc ctggggcctc tctgagactc    60
tcctgtgcag cctctggacg caccttcagt agtacaggca tgggctggtt ccgacaggct    120
ccagggaagg agcgtgaatt tgtagcagct attagcgggg atggtgatac tacatactat    180
gcagactccg tgaagggccg attcaccatc tccagagaca acgccaagaa cacggtgtat    240
ctgcaaatga acagcctgaa accgtgggac acggccgttt attactgtgc ttcgactcgg    300
ttcacatggg gcctatatag cgactttgtg aactcctatg aatatgacgc ctggggccag    360
gggaccccgg tcaccgtctc ctca                                            384
```

<210> SEQ ID NO 7
<211> LENGTH: 384
<212> TYPE: DNA
<213> ORGANISM: Artificial Sequence
<220> FEATURE:
<223> OTHER INFORMATION: synthesized

<400> SEQUENCE: 7

```
caggtgcagc tggtggagtc tgggggaggc ttggtgcaac ctgggggtc tctgagactc      60 tcctgtgcag cctctggacg caccttcagt agtacaggca tgggctggtt ccgacagggt    120
ccagggaagg agcgtgaatt tgtagcagct attagcgggg atggtgatac tacatactat    180
gcagactccg tgaagggccg attcaccatc tccagagaca acgccaagaa cacggtgtat    240
ctgcaaatga acagcctgaa acctgaggac acgccgttt attactgtgc ttcggctcgg    300
ttcacatggg gcctatatag cgactttgtg aactcctatg aatatgacgc ctggggccag    360
gggaccccgg tcaccgtctc ctca                                            384
```

<210> SEQ ID NO 8
<211> LENGTH: 384
<212> TYPE: DNA
<213> ORGANISM: Artificial Sequence
<220> FEATURE:
<223> OTHER INFORMATION: synthesized

<400> SEQUENCE: 8

```
caggtgcagc tcgtggagtc tgggggagga ttggtgcagc ctggggcctc tctgagactc      60
ttttgtgtag cctctggacg caccttcagt agtacaggca tgggctggtt ccgacaggct    120
```

```
ccagggaagg agcgtgagtt tgtagcagct attagcggtc ctggtgatac tacatactat      180
gtcgactccg tgaagggccg attcaccatc tccagagaca acgccaagaa cacggtgtat      240
ctgcaaatga acagcctgaa acctgaggac acggccgttt attactgtgc ttcggctggg      300
ttcacatggg gcctatatag cgactttgtg aactcctatg aatataacta ctggggccag      360
gggaccccgg tcaccgtctc ctca                                             384
```

```
<210> SEQ ID NO 9
<211> LENGTH: 8
<212> TYPE: PRT
<213> ORGANISM: Artificial Sequence
<220> FEATURE:
<223> OTHER INFORMATION: synthesized

<400> SEQUENCE: 9

Gly Arg Thr Leu Ser Asn Tyr Ile
1               5

<210> SEQ ID NO 10
<211> LENGTH: 8
<212> TYPE: PRT
<213> ORGANISM: Artificial Sequence
<220> FEATURE:
<223> OTHER INFORMATION: synthesized

<400> SEQUENCE: 10

Gly Arg Thr Phe Ser Ser Thr Gly
1               5

<210> SEQ ID NO 11
<211> LENGTH: 8
<212> TYPE: PRT
<213> ORGANISM: Artificial Sequence
<220> FEATURE:
<223> OTHER INFORMATION: synthesized

<400> SEQUENCE: 11

Ile Ser Arg Ser Gly Val Ile Thr
1               5

<210> SEQ ID NO 12
<211> LENGTH: 8
<212> TYPE: PRT
<213> ORGANISM: Artificial Sequence
<220> FEATURE:
<223> OTHER INFORMATION: synthesized

<400> SEQUENCE: 12

Ile Ser Gly Asp Gly Asp Thr Thr
1               5

<210> SEQ ID NO 13
<211> LENGTH: 8
<212> TYPE: PRT
<213> ORGANISM: Artificial Sequence
<220> FEATURE:
<223> OTHER INFORMATION: synthesized

<400> SEQUENCE: 13

Ile Ser Gly Pro Gly Asp Thr Thr
1               5

<210> SEQ ID NO 14
<211> LENGTH: 15
```

```
<212> TYPE: PRT
<213> ORGANISM: Artificial Sequence
<220> FEATURE:
<223> OTHER INFORMATION: synthesized

<400> SEQUENCE: 14

Ala Ala Ser Ser Ser Lys Tyr Met Ala Thr Arg Glu Tyr Asp Tyr
1               5                   10                  15

<210> SEQ ID NO 15
<211> LENGTH: 21
<212> TYPE: PRT
<213> ORGANISM: Artificial Sequence
<220> FEATURE:
<223> OTHER INFORMATION: synthesized

<400> SEQUENCE: 15

Ala Ser Thr Arg Phe Thr Trp Gly Leu Tyr Ser Asp Phe Val Asn Ser
1               5                   10                  15

Tyr Glu Tyr Asp Ala
            20

<210> SEQ ID NO 16
<211> LENGTH: 21
<212> TYPE: PRT
<213> ORGANISM: Artificial Sequence
<220> FEATURE:
<223> OTHER INFORMATION: synthesized

<400> SEQUENCE: 16

Ala Ser Ala Arg Phe Thr Trp Gly Leu Tyr Ser Asp Phe Val Asn Ser
1               5                   10                  15

Tyr Glu Tyr Asp Ala
            20

<210> SEQ ID NO 17
<211> LENGTH: 21
<212> TYPE: PRT
<213> ORGANISM: Artificial Sequence
<220> FEATURE:
<223> OTHER INFORMATION: synthesized

<400> SEQUENCE: 17

Ala Ser Ala Gly Phe Thr Trp Gly Leu Tyr Ser Asp Phe Val Asn Ser
1               5                   10                  15

Tyr Glu Tyr Asn Tyr
            20

<210> SEQ ID NO 18
<211> LENGTH: 25
<212> TYPE: PRT
<213> ORGANISM: Artificial Sequence
<220> FEATURE:
<223> OTHER INFORMATION: synthesized

<400> SEQUENCE: 18

Gln Val Gln Leu Val Glu Ser Gly Gly Gly Leu Val Gln Ala Gly Asp
1               5                   10                  15

Ser Leu Arg Leu Ala Cys Ala Ala Thr
            20                  25

<210> SEQ ID NO 19
<211> LENGTH: 25
<212> TYPE: PRT
<213> ORGANISM: Artificial Sequence
```

```
<220> FEATURE:
<223> OTHER INFORMATION: synthesized

<400> SEQUENCE: 19

Gln Val Gln Leu Val Glu Ser Gly Gly Gly Leu Val Gln Pro Gly Ala
1               5                   10                  15

Ser Leu Arg Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: synthesized

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: synthesized

<400> SEQUENCE: 21

Gln Val Gln Leu Val Glu Ser Gly Gly Gly Leu Val Gln Pro Gly Ala
1               5                   10                  15

Ser Leu Arg Leu Phe Cys Val Ala Ser
            20                  25

<210> SEQ ID NO 22
<211> LENGTH: 17
<212> TYPE: PRT
<213> ORGANISM: Artificial Sequence
<220> FEATURE:
<223> OTHER INFORMATION: synthesized

<400> SEQUENCE: 22

Met Gly Trp Phe Arg Gln Ala Pro Gly Lys Glu Pro Leu Phe Val Ala
1               5                   10                  15

Ala

<210> SEQ ID NO 23
<211> LENGTH: 17
<212> TYPE: PRT
<213> ORGANISM: Artificial Sequence
<220> FEATURE:
<223> OTHER INFORMATION: synthesized

<400> SEQUENCE: 23

Met Gly Trp Phe Arg Gln Ala Pro Gly Lys Glu Arg Glu Phe Val Ala
1               5                   10                  15

Ala

<210> SEQ ID NO 24
<211> LENGTH: 17
<212> TYPE: PRT
<213> ORGANISM: Artificial Sequence
<220> FEATURE:
```

<223> OTHER INFORMATION: synthesized

<400> SEQUENCE: 24

Met Gly Trp Phe Arg Gln Gly Pro Gly Lys Glu Arg Glu Phe Val Ala
1               5                   10                  15

Ala

<210> SEQ ID NO 25
<211> LENGTH: 38
<212> TYPE: PRT
<213> ORGANISM: Artificial Sequence
<220> FEATURE:
<223> OTHER INFORMATION: synthesized

<400> SEQUENCE: 25

Lys Tyr Ala Asp Ser Val Glu Gly Arg Phe Thr Ile Ser Arg Asp Asn
1               5                   10                  15

Ala Lys Asn Thr Ala Tyr Leu Gln Met Thr Ser Leu Glu Pro Glu Asp
            20                  25                  30

Thr Ala Val Tyr Tyr Cys
        35

<210> SEQ ID NO 26
<211> LENGTH: 38
<212> TYPE: PRT
<213> ORGANISM: Artificial Sequence
<220> FEATURE:
<223> OTHER INFORMATION: synthesized

<400> SEQUENCE: 26

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Trp Asp
            20                  25                  30

Thr Ala Val Tyr Tyr Cys
        35

<210> SEQ ID NO 27
<211> LENGTH: 38
<212> TYPE: PRT
<213> ORGANISM: Artificial Sequence
<220> FEATURE:
<223> OTHER INFORMATION: synthesized

<400> SEQUENCE: 27

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 28
<211> LENGTH: 38
<212> TYPE: PRT
<213> ORGANISM: Artificial Sequence
<220> FEATURE:
<223> OTHER INFORMATION: synthesized

<400> SEQUENCE: 28

Tyr Tyr Val Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 29
<211> LENGTH: 11
<212> TYPE: PRT
<213> ORGANISM: Artificial Sequence
<220> FEATURE:
<223> OTHER INFORMATION: synthesized

<400> SEQUENCE: 29

Trp Gly Gln Gly Thr Gln Val Thr Val Ser Ser
1               5                   10

<210> SEQ ID NO 30
<211> LENGTH: 20
<212> TYPE: DNA
<213> ORGANISM: Artificial Sequence
<220> FEATURE:
<223> OTHER INFORMATION: synthesized

<400> SEQUENCE: 30
caggtgaagg tcatcgartc                                           20

<210> SEQ ID NO 31
<211> LENGTH: 23
<212> TYPE: DNA
<213> ORGANISM: Artificial Sequence
<220> FEATURE:
<223> OTHER INFORMATION: synthesized

<400> SEQUENCE: 31
gatgctcttg tgactcagga atc                                       23

<210> SEQ ID NO 32
<211> LENGTH: 55
<212> TYPE: DNA
<213> ORGANISM: Artificial Sequence
<220> FEATURE:
<223> OTHER INFORMATION: synthesized

<400> SEQUENCE: 32
ggaattccat atggattata aagatgatga taaacgcaga gacagtgacc agagt    55

<210> SEQ ID NO 33
<211> LENGTH: 57
<212> TYPE: DNA
<213> ORGANISM: Artificial Sequence
<220> FEATURE:
<223> OTHER INFORMATION: synthesized

<400> SEQUENCE: 33
ggaattccat atggattata aagatgatga taaacaggtc accttgaagg agtctgg  57

<210> SEQ ID NO 34
<211> LENGTH: 57
<212> TYPE: DNA
<213> ORGANISM: Artificial Sequence
<220> FEATURE:
<223> OTHER INFORMATION: synthesized

<400> SEQUENCE: 34
ggaattccat atggattata aagatgatga taaacaggtg cagctgcagg agtcggg  57

```
<210> SEQ ID NO 35
<211> LENGTH: 45
<212> TYPE: DNA
<213> ORGANISM: Artificial Sequence
<220> FEATURE:
<223> OTHER INFORMATION: synthesized

<400> SEQUENCE: 35
ccacgattct gcggccgctt actgaggaga cagtgacctg ggtcc            45
```

NANO ANTIBODY FOR NEUTRALIZING TOXICITY OF SARS-CoV-2 AND PREPARATION METHOD AND APPLICATION THEREOF

CROSS-REFERENCE TO RELATED APPLICATIONS

The present application is a national phase entry under 35 USC § 371 of International Application PCT/CN2020/132279, filed Nov. 27, 2020, which claims the benefit of and priority to Chinese Patent Application No. 2020109267723, filed Sep. 7, 2020, the entire disclosures of which are incorporated herein by reference.

FIELD OF THE INVENTION

The present disclosure relates to the field of polypeptide technologies, and more particularly, to a nano antibody for neutralizing a toxicity of SARS-CoV-2 and preparation method and application thereof.

BACKGROUND OF THE INVENTION

Corona Virus Disease 2019 (COVID-19) is caused by a novel R coronavirus-SARS-CoV-2, which uses an angiotensin converting enzyme 2 (ACE-2) as a receptor to invade cells, resulting in lung injury. The aggravation of Corona Virus Disease 2019 is closely related to a systemic inflammatory response caused by secondary onset. Critical patients will suffer from acute respiratory distress syndrome (ARDS) and septic shock, and will finally suffer from multiple organ failure. At present, most therapeutic drugs, such as baricitinib, remdesivir, chloroquine, and the like, are still in a clinical trial stage, and there is no specific drug used for treatment. The COVID-19 is highly contagious, and may cause many serious complications, thus posing a great threat to global public safety.

Research and development of a vaccine for SARS-CoV-2 is an important method for virus prevention and control. However, due to a long verification period of a vaccine safety and efficacy experiment, it usually takes at least 1 to 2 years to complete evaluation, so that no effective vaccine has entered the market and been widely used so far. Even a recombinant fully-humanized monoclonal antibody has the disadvantages of immunogenicity, a high production cost, and the like.

A neutralizing antibody is a kind of antibody with a protective effect which is produced by a body in response to antigen stimulation, and the neutralizing antibody may be a useful treatment method even in a relatively late stage of the disease. As a supplement to the vaccine and chemotherapy, an antibody-mediated measure for preventing and treating viral infection has shown good effects, and application prospects thereof have been recognized by experts. At present, there have been successfully cured cases of transfusing plasma from rehabilitated COVID-19 patients to severe patients. However, polyclonal antibody plasma is not only limited in source, but also limited in clinical application by conditions, such as difficulty in quality control, mismatched blood types of a donor and a recipient, a potential infectious factor, and the like, while a humanized monoclonal antibody may effectively overcome the above problems. Therefore, research and development of a neutralizing antibody of SARS-CoV-2 can accelerate clinical evaluation of an antibody drug of SARS-CoV-2, and enhance the treatment and prevention measures of the COVID-19.

SUMMARY OF THE INVENTION

The present disclosure aims to solve at least one of the technical problems in the prior art. For this purpose, the present disclosure provides a nano antibody for neutralizing the toxicity of SARS-CoV-2, which can be used for preventing and treating COVID-19.

The present disclosure further provides a preparation method of the above nano antibody for neutralizing the toxicity of SARS-CoV-2.

The present disclosure further provides an application of the above nano antibody for neutralizing the toxicity of SARS-CoV-2.

The present disclosure further provides a gene encoding a nano antibody for neutralizing the toxicity of SARS-CoV-2.

The present disclosure further provides a recombinant plasmid.

The present disclosure further provides a recombinant cell.

In the first aspect, according to an embodiment of the present disclosure, a nano antibody for neutralizing the toxicity of SARS-CoV-2 is provided, and the nano antibody comprises a framework region FR and a complementarity determining region CDR, wherein the complementarity determining region CDR comprises a CDR1, a CDR2 and a CDR3;

an amino acid sequence of the CDR1 is selected from at least one of the amino acid sequences shown in SEQ ID NO: 9 and SEQ ID NO: 10;

an amino acid sequence of the CDR2 is selected from at least one of the amino acid sequences shown in SEQ ID NO: 11, SEQ ID NO: 12, and SEQ ID NO: 13; and an amino acid sequence of the CDR3 is selected from at least one of the amino acid sequences shown in SEQ ID NO: 14, SEQ ID NO: 15, SEQ ID NO: 16, and SEQ ID NO: 17.

The nano antibody for inhibiting SARS-CoV-2 infection according to the embodiment of the present disclosure has at least the following beneficial effects:

the nano antibody for neutralizing the toxicity of SARS-CoV-2 according to the present disclosure has the advantages of a small molecular weight (only 1/10 of that of a monoclonal antibody), a high binding activity (a high affinity with SARS-CoV-2), a low production cost, and the like; the nano antibody according to the present disclosure has a strong inhibition ability to the virus at a high concentration, such as an inhibition rate as high as 100% at a concentration of 1 g/ml, and has a strong neutralizing ability to a SARS-CoV-2 pseudovirus, and a strong antiviral effect; and the nano antibody according to the present disclosure also has a mature preclinical effectiveness, a safety research foundation, and a high success rate of industrialized transformation, and can quickly enter clinical research.

According to some embodiments of the present disclosure, the amino acid sequence of the complementarity determining region CDR is any one of the following (1) to (4): (1) the CDR1 shown in SEQ ID NO: 9, the CDR2 shown in SEQ ID NO: 11, and the CDR3 shown in SEQ ID NO: 14; (2) the CDR1 shown in SEQ ID NO: 10, the CDR2 shown in SEQ ID NO: 12, and the CDR3 shown in SEQ ID NO: 15; (3) the CDR1 shown in SEQ ID NO: 10, the CDR2 shown in SEQ ID NO: 12, and the CDR3 shown in SEQ ID NO: 16;

and (4) the CDR1 shown in SEQ ID NO: 10, the CDR2 shown in SEQ ID NO: 13, and the CDR3 shown in SEQ ID NO: 17.

According to some embodiments of the present disclosure, the nano antibody further comprises a framework region FR, wherein the framework region FR comprises a FR1, a FR2, a FR3 and a FR4;

an amino acid sequence of the FR1 is selected from at least one of the amino acid sequences shown in SEQ ID NO: 18, SEQ ID NO: 19, SEQ ID NO: 20, and SEQ ID NO: 21;

an amino acid sequence of the FR2 is selected from at least one of the amino acid sequences shown in SEQ ID NO: 22, SEQ ID NO: 23, and SEQ ID NO: 24;

an amino acid sequence of the FR3 is selected from at least one of the amino acid sequences shown in SEQ ID NO: 25, SEQ ID NO: 26, SEQ ID NO: 27, and SEQ ID NO: 28; and an amino acid sequence of the FR4 is shown in SEQ ID NO: 29.

Further, the amino acid sequence of the framework region FR is any one of the following (1) to (4): (1) the FR1 shown in SEQ ID NO: 18, the FR2 shown in SEQ ID NO: 22, the FR3 shown in SEQ ID NO: 25, and the FR4 shown in SEQ ID NO: 29; (2) the FR1 shown in SEQ ID NO: 17, the FR2 shown in SEQ ID NO: 23, the FR3 shown in SEQ ID NO: 26, and the FR4 shown in SEQ ID NO: 29; (3) the FR1 shown in SEQ ID NO: 20, the FR2 shown in SEQ ID NO: 24, the FR3 shown in SEQ ID NO: 27, and the FR4 shown in SEQ ID NO: 29; and (4) the FR1 shown in SEQ ID NO: 21, the FR2 shown in SEQ ID NO: 23, the FR3 shown in SEQ ID NO: 28, and the FR4 shown in SEQ ID NO: 29.

According to some embodiments of the present disclosure, an amino acid sequence of the nano antibody is the amino acid sequence shown in SEQ ID NO: 1, SEQ ID NO: 2, SEQ ID NO: 3 or SEQ ID NO: 4.

According to some embodiments of the present disclosure, the nano antibody is an amino acid sequence which has a high affinity with a SARS-CoV-2 RBD protein, and the high affinity refers to that a $K_D$ value that is between $1 \times 10^{-12}$ and $1 \times 10^{-6}$.

In the second aspect, according to an embodiment of the present disclosure, a preparation method of the nano antibody for neutralizing the toxicity of SARS-CoV-2 is provided, comprising the following steps:

(1) cloning a nucleotide sequence shown in SEQ ID NO: 5, SEQ ID NO: 6, SEQ ID NO: 7 or SEQ ID NO: 8 into an expression vector to obtain a recombinant plasmid, and transferring the recombinant plasmid into a host cell, inducing, to express the nano antibody; and (2) purifying the nano antibody from the host cell.

The preparation method according to the embodiment of the present disclosure has at least the following beneficial effects: a fermentation system used in the preparation method of the present disclosure is simple and easy to industrialize.

According to some embodiments of the present disclosure, a screening method of the nucleotide sequence of the nano antibody comprises the following steps of:

(1) using S1 protein to immunize a llama, extracting total mRNA from a peripheral blood mononuclear cell, and reversely transcribing the mRNA into cDNA; and (2) amplifying a variable region gene of a heavy chain antibody through a PCR, constructing a variable region phage display library of the heavy chain antibody, screening and sequencing to obtain a nucleotide sequence capable of expressing the nano antibody.

In the third aspect, according to an embodiment of the present disclosure, applications of a nano antibody for neutralizing the toxicity of SARS-CoV-2 comprise the following aspects:

an application of the nano antibody in the manufacture of a medicament for preventing and/or treating COVID-19; and/or an application of the nano antibody in the manufacture of a detection reagent for detecting the SARS-CoV-2; and/or an application of the nano antibody in the manufacture of a detection kit for detecting the SARS-CoV-2.

The applications according to the embodiments of the present disclosure have at least the following beneficial effects: the nano antibody according to the present disclosure has good neutralizing activity and inhibition activity for SARS-CoV-2, and is suitable for preventing and/or treating COVID-19; and meanwhile, the nano antibody has a high affinity with the SARS-CoV-2, and can be detected by binding to the SARS-CoV-2.

In the fourth aspect, according to an embodiment of the present disclosure, a gene encoding a nano antibody for neutralizing the toxicity of SARS-CoV-2 is provided, wherein a nucleotide sequence of the gene is shown in SEQ ID NO: 5, SEQ ID NO: 6, SEQ ID NO: 7 or SEQ ID NO: 8.

In the fifth aspect, according to an embodiment of the present disclosure, a recombinant plasmid is provided, wherein the recombinant plasmid comprises at least one of the gene fragments of nucleotide sequences shown in SEQ ID NO: 5, SEQ ID NO: 6, SEQ ID NO: 7 or SEQ ID NO: 8.

In the sixth aspect, according to an embodiment of the present disclosure, a recombinant cell is provided, wherein the recombinant cell comprises at least one of the gene fragments of nucleotide sequences shown in SEQ ID NO: 5, SEQ ID NO: 6, SEQ ID NO: 7 or SEQ ID NO: 8.

The additional aspects and advantages of the present disclosure will be partially provided in the following description, and will partially be apparent in the following description, or learned by practice of the present disclosure.

BRIEF DESCRIPTION OF THE DRAWINGS

FIG. 1 is a flowchart of an embodiment of the present disclosure;

DETAILED DESCRIPTION OF THE EMBODIMENTS

In order to describe the technical contents, the objectives and the effects of the present disclosure in detail, the description will be made with reference to the embodiments and the accompanying drawings hereinafter.

An experimental flowchart of one embodiment of the present disclosure is shown in FIG. 1, which comprises: purchasing S1 protein to immunize a llama; collecting a large amount of blood, and separating a peripheral blood mononuclear cell (PBMC) of the llama; extracting mRNA, and reversely transcribing the mRNA into cDNA; designing a primer independently, and amplifying a heavy chain variable region of an antibody through a two-step PCR; constructing a phage display library of the heavy chain variable region of the antibody (a capacity of the immune library is $10^8$); screening the library for 2 to 3 rounds, and carrying out sequencing; directly constructing an ELISA positive clone into an *Escherichia coli* expression vector for small expression; and carrying out a virus neutralization test on samples subjected to small expression to obtain a group of nano antibodies capable of neutralizing SARS-CoV-2.

S1 protein: the S1 protein has a full name of spike glycoprotein, and is located at an outermost layer of the SARS-CoV-2 like a raised "crown". Coronavirus was named because of this.

The S1 protein used in the examples of the present disclosure was purchased from SinoBiological Biotechnology Co., Ltd., with an item number of 40591-V08H 2019-nCoV Spike Protein S1 (His Tag).

Example 1 Preparation of the Nano Antibody for Inhibiting SARS-CoV-2 Infection 1. Methods and Results of Animal Immunization Immune methods for llama: an adult male healthy llama, numbered KZL007, was immunized by subcutaneous multi-point injection. Every 14 days, 0.9 mg of S1 protein was injected every time, three times in total. 2 ml of blood was collected to measure a potency, 14 days after immunization for the third time.

Method for detecting the immune potency of llama: enzyme-linked immunosorbent assay was used, a target antigen was a SARS-CoV-2 RBD protein, a primary antibody was anti-his-HRP, TMB was used for color development, and an O.D. value at 450 nm was detected. When serum was diluted by 128K times (i.e., 128,000 times, which was similar in meaning hereinafter), if an ELISA result was larger than 1.0, the immunization may be considered to be successful. The serum was diluted with a PBS buffer with a pH 7.4 during detection, wherein the serum was diluted by 1K times, 2K times, 4K times, 8K times, 16K times, 32K times, 64K times, 128K times, 256K times, 512K times, 1024K times, 2048K times, 4096K times, 8192K times, and 16384K times.

Figure 2:
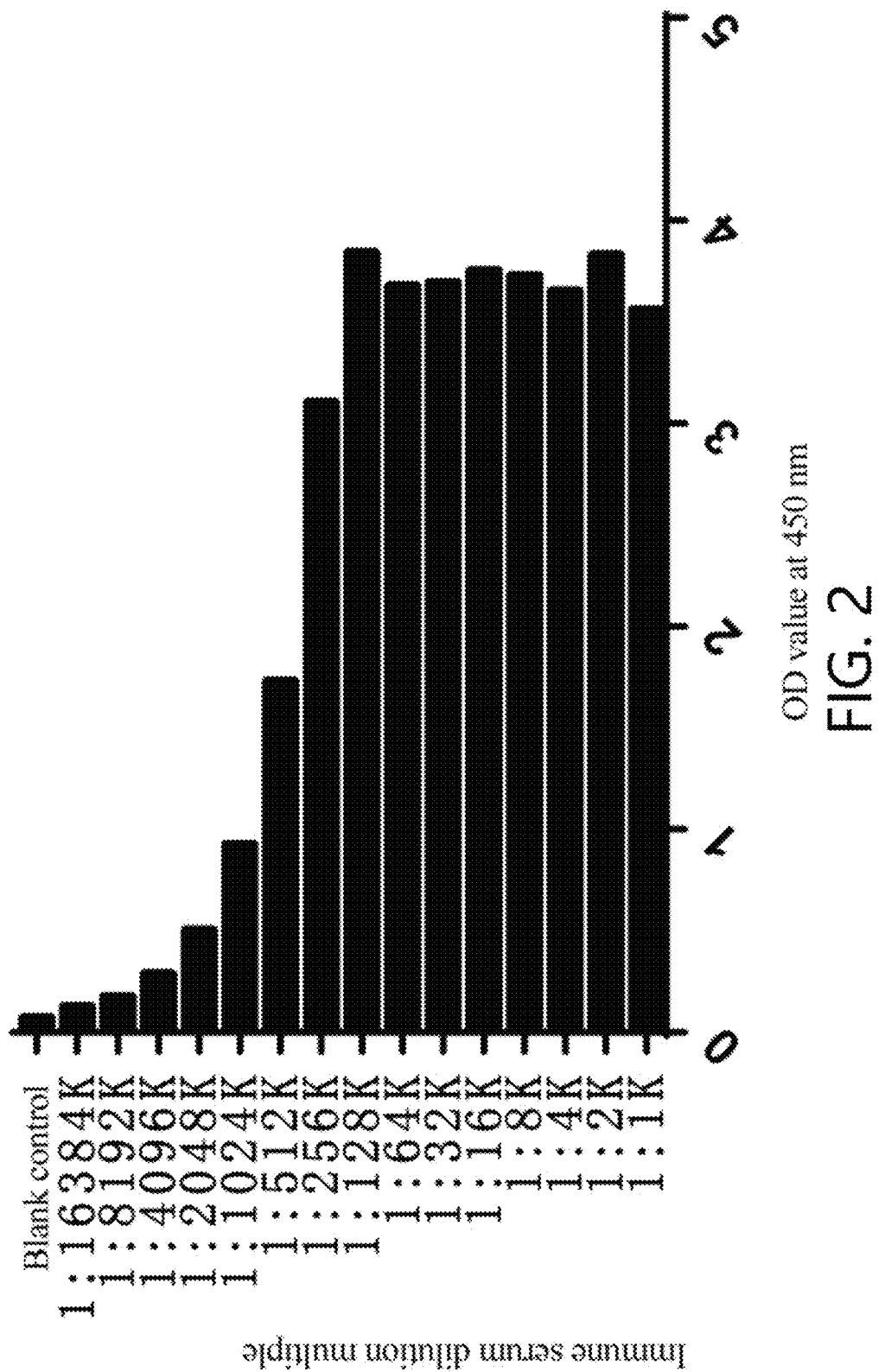
FIG. 2 shows a detection result of an immunizing potency of a llama according to Example 1 of the present disclosure.

FIG. 2 shows a detection result of the immunizing potency of the llama, and it can be seen from FIG. 2 that:

1) Generally, if an $OD_{450}$ value of the immunizing potency is larger than 1 at 128K, the immunization may be considered to be successful, and the immunization may be stopped. The immunizing potency in the present disclosure reaches a serum dilution multiple of 1024K, which far exceeds a common value in the industry.

2) The blank control value is normal. The reason why the $OD_{450}$ reading did not change much from a serum dilution ratio of 1:1K to a serum dilution ratio of 1:128K is that the antibody concentration in the serum was too high, resulting in an excessively large potency and reaching the maximum reading range of the instrument. However, the data shows a normal gradient decline from a dilution ratio of 256K.

2. Methods and Results for Obtaining mRNA and cDNA

Method for obtaining mRNA: a large amount of blood was collected from the llama meeting potency requirements, PBMCs were separated, and total RNA was extracted from $17 \times 10^6$ PBMCs. An extraction method of the total RNA was manual extraction with TRIZOL®. Specific operation was as follows: the separated PBMCs were taken out from a liquid nitrogen tank, and thawed quickly; 800 g of the separated PBMCs were centrifuged for 5 minutes, a supernatant was discarded, and a precipitate was obtained; 1 mL of TRIZOL® solution was added into the precipitate, and the mixture was gently blown and beaten back and forth for several times with a gun to fully lyse the cells; 200 μl of chloroform was added, shaken violently for 30 seconds, stood for 5 minutes, centrifuged at 13,500 r/min for 10 minutes, and layered; an upper liquid phase was sucked into another new 1.5 mL RNase-free tube, and an equal volume of isopropanol was added; the mixture was mixed evenly, and precipitated at −20° C. for 20 minutes to obtain a precipitated liquid; the precipitated liquid was centrifuged at 13,500 r/min for 10 minutes, the supernatant was discarded, and a precipitate was obtained; the precipitate was rinsed twice with 75% ice ethanol, blown and dried with a super clean bench, and redissolved with 60 μl of RNase-free water for later use.

Figure 3:
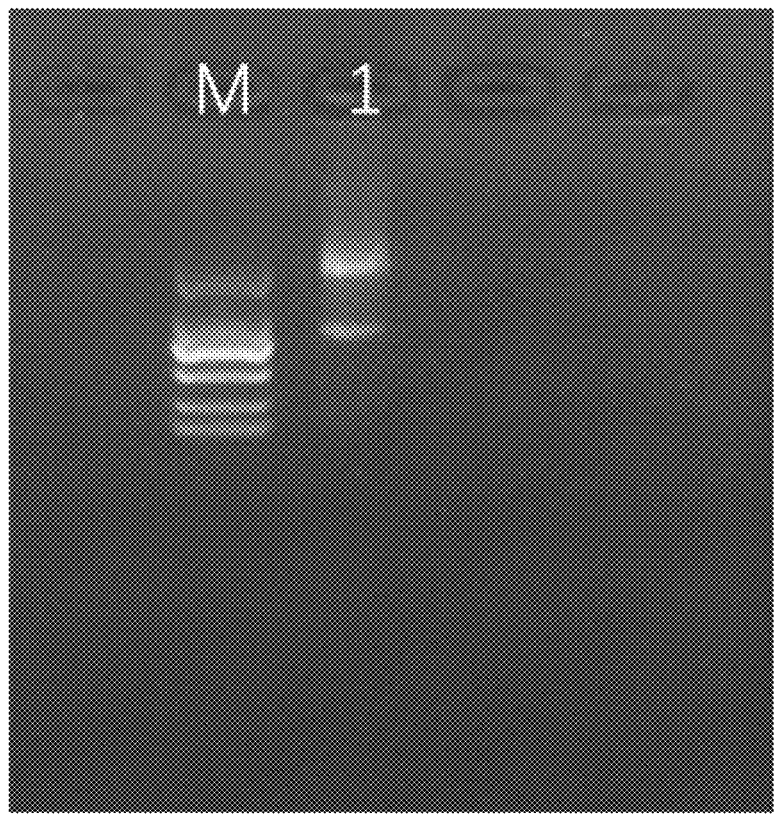
FIG. 3 is an electrophoresis diagram of total RNA of a PBMC of the llama according to Example 1 of the present disclosure.

An electrophoresis diagram of RNA obtained is shown in FIG. 3, wherein M refers to a DNA maker DL2000 (2,000 bp, 1,000 bp, 750 bp, 500 bp, 250 bp, and 100 bp); and Lane 1 refers to RNA of the PBMC of the immunized llama (28S and 16S). A 28S band and a 16S band of the mRNA can be clearly seen from the figure, indicating that the RNA is successfully acquired in the present disclosure.

Method for obtaining cDNA: the total RNA was reversely transcribed into the cDNA with a reverse transcription kit purchased from Thermo company, the cDNA was quantified and packaged, and stored at −80° C. for later use.

3. Method and Result of Obtaining Nano Antibody Nucleic Acid Fragments

Two-step PCR amplification was carried out by using primers in Table 1 below to acquire a target fragment.

TABLE 1

Primers for Constructing Phage Library

| Primer name | Primer sequence |
|---|---|
| Kz-001 (SEQ ID NO. 30) | CAGGTGAAGGTCATCGARTC |
| Kz-002 (SEQ ID NO. 31) | GATGCTCTTGTGACTCAGGAATC |
| Kz-003 (SEQ ID NO. 32) | GGAATTCCATATGGATTATAAAGAT GATGATAAACGCAGAGACAGTGACC AGAGT |
| Kz-004 (SEQ ID NO. 33) | GGAATTCCATATGGATTATAAAGAT GATGATAAACAGGTCACCTTGAAGG AGTCTGG |
| Kz-005 (SEQ ID NO. 34) | GGAATTCCATATGGATTATAAAGAT GATGATAAACAGGTGCAGCTGCAGG AGTCGGG |
| Kz-006 (SEQ ID NO. 35) | CCACGATTCTGCGGCCGCTTACTGA GGAGACAGTGACCTGGGTCC |

A PCR reaction procedure was as follows:

A first round of PCR was carried out by using Kz-001 and Kz-002 as primers, the amplification was carried out with a high-fidelity PCR polymerase from TAKARA company, and the amplification procedure was as follows: pre-denaturing at 94° C. for 3 minutes; denaturing at 94° C. for 30 seconds, annealing at 53° C. for 30 seconds, extending at 72° C. for 40 seconds, and circulating the procedure for 18 rounds; extending at a tail end at 72° C. for 10 minutes; and cooling at 4° C. for 1 minute. A 750 bp band was recovered.

A second round of PCR was carried out by using Kz-003, Kz-004 and Kz-006 as primers, the amplification was carried out with a high-fidelity PCR polymerase from TAKARA company, and the amplification procedure was as follows: pre-denaturing at 94° C. for 3 minutes; denaturing at 94° C. for 30 seconds, annealing at 53° C. for 30 seconds, extending at 72° C. for 40 seconds, and circulating the procedure for 20 rounds; extending at a tail end at 72° C. for 10 minutes; and cooling at 4° C. for 1 minute. A 450 bp band was recovered.

Figure 4:
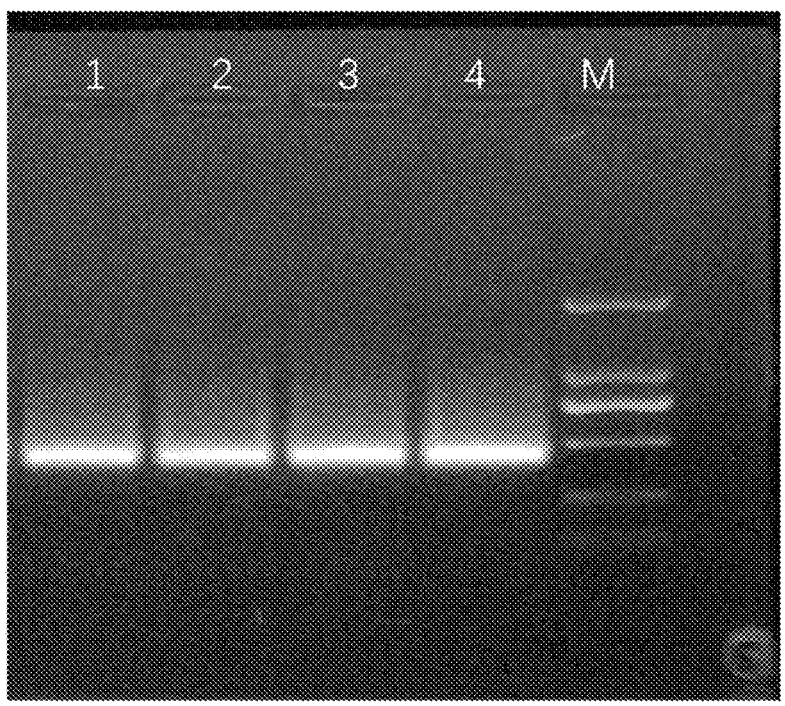
FIG. 4 shows agarose gel electrophoresis obtained by a nucleic acid fragment of a nano antibody according to Example 1 of the present disclosure.

A result of the second round of PCR (agarose gel electrophoresis diagram of the nucleic acid fragment of the nano antibody) is shown in FIG. 4, wherein M refers to a DNA maker DL2000 (2,000 bp, 1,000 bp, 750 bp, 500 bp, 250 bp, and 100 bp); and Lane 1 to Lane 4 refer to a second round of PCR agarose gel electrophoresis. A specific target band with a size of 450 bp can be clearly seen from FIG. 4, which is a fragment of the nano antibody. These bands were recovered with an agarose gel recovery kit and quantified.

4. Phage Display Solution

Restriction enzyme digestion was carried out on the nucleic acid fragment of the nano antibody above, wherein two restriction enzyme digestion sites used in the examples of the present disclosure were sfiI and NotI, and the nucleic acid fragment was recovered with a gel recovery kit and then quantified. A commercial vector pCANTAB 5E was used in the examples of the present disclosure, and in the meanwhile, the vector was also subjected to the above two restriction enzyme digestions, and was recovered with a gel recovery kit and then quantified. After restriction enzyme digestion, a concentration of the fragment was 120 ng/μl, and a concentration of the vector was 80 ng/μl.

Figure 5:
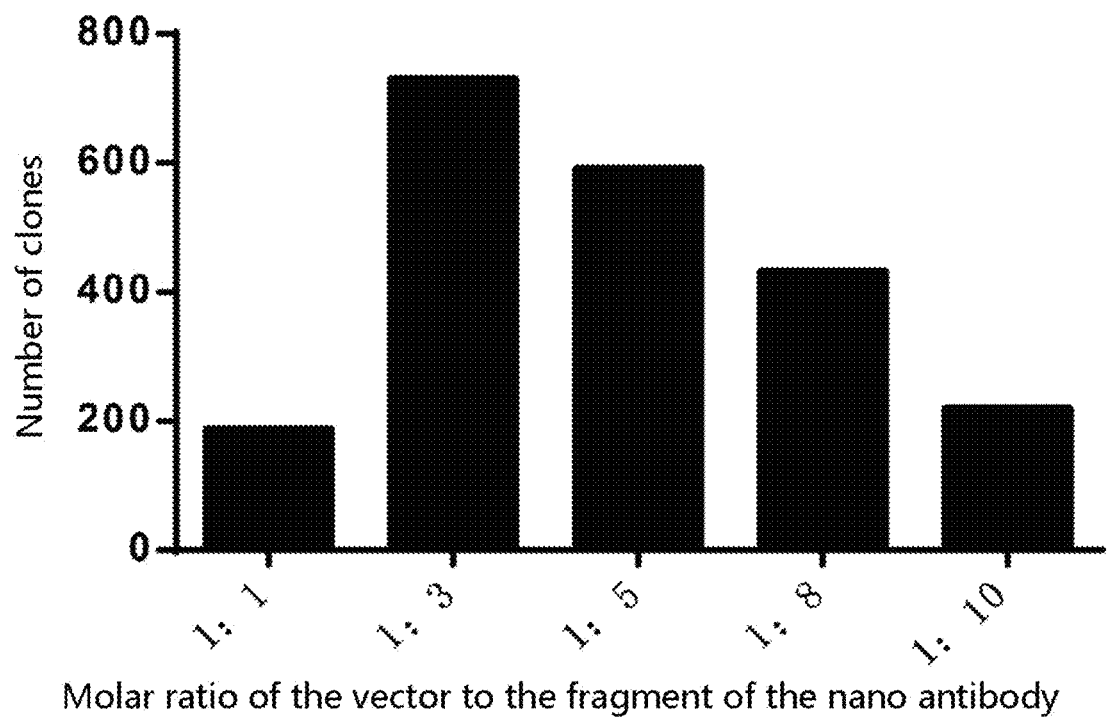
FIG. 5 is an exploring result diagram of a connecting condition of a phage display library according to Example 1 of the present disclosure.

The exploration results of the connection conditions for constructing a phage display library in the example of the present disclosure are shown in FIG. 5, and it can be seen from FIG. 5 that an overnight connecting efficiency is maximum when a molar ratio of the vector to the fragment of the nano antibody is 1:3 in a 10 μl connecting system.

All vectors subjected to restriction enzyme digestion and all fragments of the nano antibody subjected to restriction enzyme digestion were connected overnight with the molar ratio of 1:3, transformed into TG1 competent cells by electric shock, diluted and spread on a plate, and then the number of clones was counted to obtain a phage display library of $3.4 \times 10^8$.

5. Screening Method and Result of Phage

A screening method of the phage display library in the present disclosure was as follows: a solid-phase screening method was used to screen the phage library. A screening process was as follows: target molecules were coated on surfaces of 96 wells, un-adsorbed target molecules were washed off, then the wells were sealed, and then a phage antibody library subjected to background correction was added into the wells for binding; unbound phage was washed off, and eluted with 0.2 M glycine-hydrochloric acid to obtain an affinity phage. The phage with a high affinity was obtained by reducing a concentration of the coated target molecules and increasing a washing strength in each round (in the example of the present disclosure, the phage with a high affinity was obtained by reducing the concentration of the target molecules and increasing a Tween 20 concentration of the washing solution). After each round of screening and amplification tests, the nano antibodies capable of binding to the target molecules could be gathered in the phage library. After three rounds of screening, the gathering reached more than 1,000 times, and a monoclone was selected for verification. Results of three rounds of screening are shown in Table 2 below:

TABLE 2

Screening Result of Phage Display Library of Anti-SARS-CoV-2 Nano Antibody

| Number of rounds of screening | Input (pfu) | Output (pfu) | Gathering rate (input/output) |
|---|---|---|---|
| First round | $3 \times 10^{11}$ | $9.48 \times 10^6$ | $3.16 \times 10^4$ |
| Second round | $3 \times 10^{11}$ | $4.47 \times 10^7$ | $6.71 \times 10^3$ |
| Third round | $3 \times 10^{11}$ | $6.81 \times 10^8$ | $4.4 \times 10^2$ |

6. ELISA Binding Detection Solution and Result 768 monoclones were selected from products of three rounds of screening for ELISA identification. An ELISA identification method was as follows: a target protein was diluted with a coating solution having a pH of 9.6, stood at 37° C. for 1 hour, coated, and then washed with PBS three times. A confining liquid was added for confining, stood at 37° C. for 1 hour, and washed with PBS three times after excess confining liquid was thrown away. Amplification products were diluted by 10 times with 1% M-PBS, mixed evenly, divided into 50p/well, and stood at 37° C. for 1 hour. Primary antibody: rabbit anti-M13 was diluted with 1% M-PBS at 1:1,000, divided into 50 μl/well, and stood at 37° C. for 1.0 hour. Secondary antibody: HRP-goat anti-rabbit was diluted with 1% M-PBS at 1:3,000, divided into 50 μl/well, and stood at 37° C. for 1.0 hour. Color development: 4.5 ml of 0.2 M/L $Na_2HPO_4$ and 4.5 ml of 0.1 M/L citric acid were respectively added with a small amount of OPD (o-phenylenediamine), and mixed evenly with 60 μl of $H_2O_2$, and divided into 50 μl/well. Termination was carried out by adding 50 μl 2 M sulfuric acid into per well. Detection was carried out at 490 nm. Phage ELISA was repeated at least once. Storage of positive clone: 0.5 ml of phase and 0.3 ml of 50% glycerol were mixed evenly, and stored at −80° C.

Figure 6:
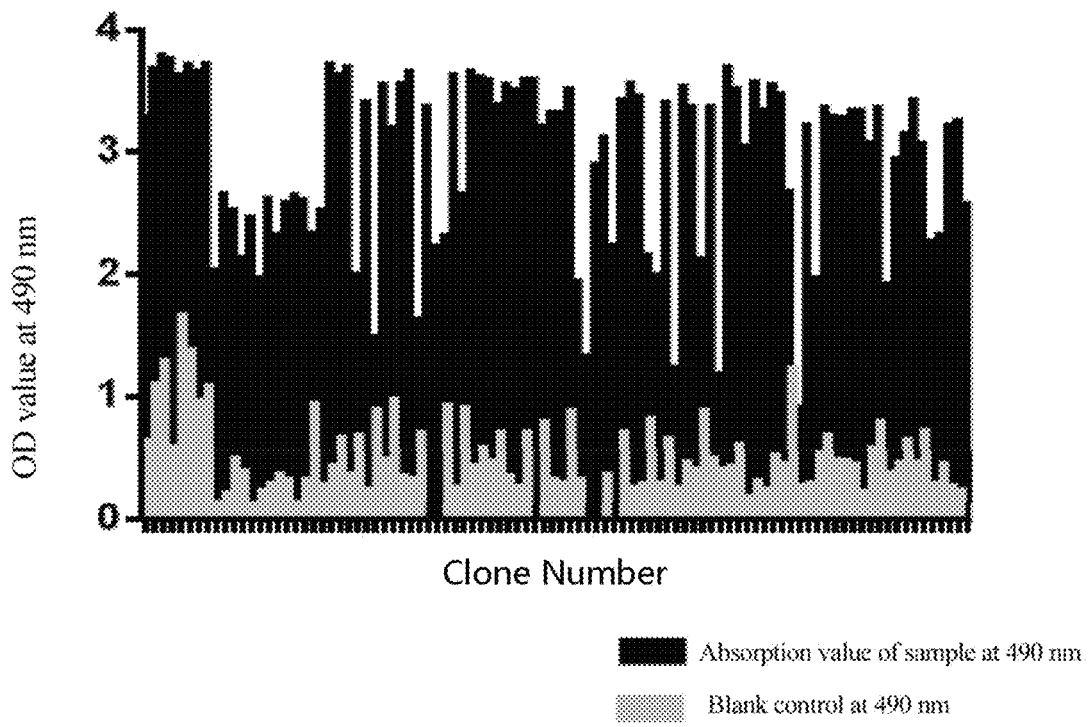
FIG. 6 is an ELISA result diagram of nucleotide sequences of different nano antibodies screened according to Example 1 of the present disclosure.

Positive sequences in the ELISA were sequenced to obtain nucleotide sequences of different nano antibodies. ELISA results of the sequences are shown in FIG. 6 (an x-coordinate corresponds to the nucleotide sequence of each nano antibody, and a y-coordinate represents an absorption intensity at 490 nm). It can be seen from FIG. 6 that absorption values of all screened sequences at 490 nm are much larger than those of the blank control group, indicating that a result of the binding of nano-antibody to the RBD protein is positive. In the example, four different nano sequences were selected from positive sequences for follow-up research.

7. Construction Method and Result of Expression Strain

Construction method of expression strain: the sequence of the nano antibody was amplified by a PCR; NdeI and XhoI enzyme digestion sites were introduced at two ends of the fragment of the nano antibody, and the two enzyme digestion sites were connected to a PET30A vector; and the sequence was correct in sequencing for later use.

8. Method for Obtaining Trace Sample

Successfully constructed clones NBS1-2, NBS1-3, NBS1-10 and NBS1-57 were induced to express in *Escherichia coli* BL21 (DE3) with 1 mM IPTG at 37° C. overnight, renatured and purified to a sample with a purity not less than 95%.

The specific steps of induced expression, purification and renaturation were as follows:

1) After inoculation, IPTG was added when an $OD_{600}$ value was 0.5, so that a final concentration of the IPTG was 1 mM, and the mixture was induced at 37° C. overnight.
2) After induced expression, bacteria were collected by centrifugation, and homogenized and disrupted.
3) An inclusion body was washed with a Tris® buffer, weighed, and added with a denaturing solution; the inclusion body was dissolved according to a ratio of 1 g of inclusion body to 15 ml of denaturing solution.

Wherein, a formula of the denaturing solution was: 4 M guanidine hydrochloride or 6 M urea (or using alkaline denaturing), and a redox couple (comprising but not limited to GSH/GSSG, cystine/cysteine, and the like), pH 9.0.

Figure 7:
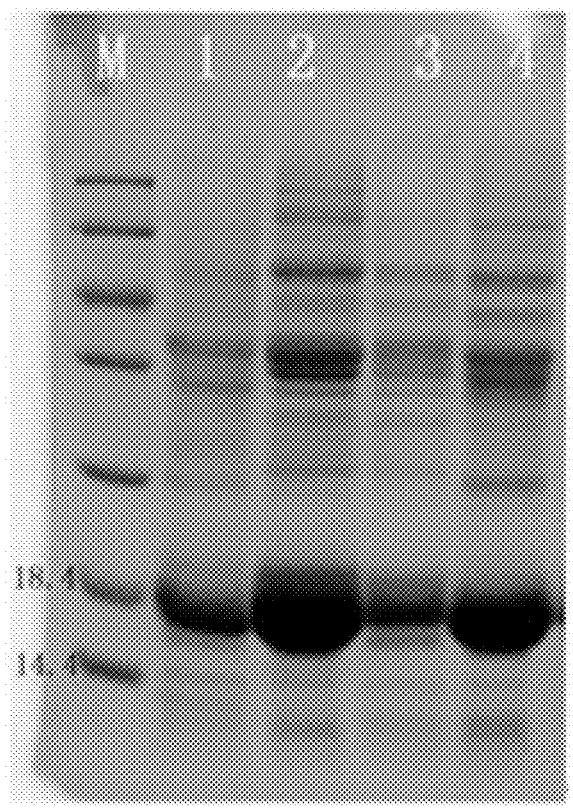
FIG. 7 is an electrophoresis diagram of a protein of a purified nano antibody according to Example 1 of the present disclosure.

4) The dissolved inclusion body was processed, comprising but being not limited to centrifugation, dialysis to remove an oxidant, a reducing agent or a redox couple, purification, and the like.
5) The processed inclusion body dissolving liquid was subjected to renaturation, comprising pulse renaturation, dilution renaturation, and the like. The renaturation was carried out at a low temperature (4° C.) or a room temperature (25° C.) for 24 hours. A formula of a renaturing solution was: 2 M urea, and a redox couple (comprising but being not limited to GSH/GSSG, cystine/cysteine, and the like), pH 9.0.
6) A renatured sample was processed, comprising but not limited to centrifugation, pH adjustment, filtration/ultra-filtration, liquid exchange concentration, and the like.
7) The processed renaturing solution was purified, and chromatographed with cation or anion resin.
8) Gel chromatography was carried out on a collected target eluted protein, and a target protein peak was collected. SDS-PAGE gel running observation was carried out on the processed renaturing solution. FIG. 7 is an electrophoresis diagram (SDS-PAGE) of a purified nano antibody, where M refers to a marker; 1 refers to NBS1-2; 2 refers to NBS 1-3; 3 refers to NBS1-10; and 4 refers to NBS1-57. It can be seen from FIG. 7 that the purity of the sample is larger than 80%.

Sequence information of four nano antibodies (NBS1-2, NBS1-3, NBS1-10, and NBS1-57) inhibiting the SARS-CoV-2 in the example of the present disclosure was as follows:

i. Specifically, amino acid sequences of the nano antibodies were as follows:

1) amino acid sequence of NBS1-2 (SEQ ID NO. 1):
QVQLVESGGGLVQAGDSLRLACAATGRTLSNYIMGWFRQAPGKEPLFVA

AISRSGVITKYADSVEGRFTISRDNAKNTAYLQMTSLEPEDTAVYYCAA

SSSKYMATREYDYWGQGTQVTVSS;

2) amino acid sequence of NBS1-3 (SEQ ID NO. 2):
QVQLVESGGGLVQPGASLRLSCAASGRTFSSTGMGWFRQAPGKEREFVA

AISGDGDTTYYADSVKGRFTISRDNAKNTVYLQMNSLKPWDTAVYYCAS

TRFTWGLYSDFVNSYEYDAWGQGTPVTVSS;

3) amino acid sequence of NBS1-10 (SEQ ID NO. 3):
QVQLVESGGGLVQPGGSLRLSCAASGRTFSSTGMGWFRQGPGKEREFVA

DAISGGDTTYYADSVKGRFTISRDNAKNTVYLQMNSLKPEDTAVYYCAS

ARFTWGLYSDFVNSYEYDAWGQGTPVTVSS;
and 4) amino acid sequence of NBS1-57 (SEQ ID NO. 4):
QVQLVESGGGLVQPGASLRLFCVASGRTFSSTGMGWFRQAPGKEREFVA

AISGPGDTTYYVDSVKGRFTISRDNAKNTVYLQMNSLKPEDTAVYYCAS

AGFTWGLYSDFVNSYEYNYWGQGTPVTVSS ii. Specifically, nucleotide sequences of the nano antibodies were as follows:

1) nucleotide sequence of NBS1-2 (SEQ ID NO. 5):
CAGGTGCAGCTCGTGGAGTCTGGGGGAGGATTGGTGCAGGCTGGGGACT

CTCTGAGACTCGCCTGTGCAGCCACTGGACGCACCCTCAGTAACTATAT

CATGGGCTGGTTCCGCCAGGCTCCAGGAAAGGAACCTTTGTTTGTAGCA

GCAATTAGCCGGAGTGGTGTCATCACAAAGTATGCAGACTCCGTAGAGG

GCCGATTCACCATCTCCAGAGACAATGCCAAGAACACGGCGTATCTGCA

GATGACTAGTCTGGAACCTGAAGACACGGCCGTCTATTATTGTGCAGCA

TCGTCTAGTAAATACATGGCTACGCGAGAGTATGACTACTGGGGCCAGG

GGACCCAGGTCACCGTCTCCTCA;

2) nucleotide sequence of NBS1-3 (SEQ ID NO. 6):
CAGGTGCAGCTGGTGGAGTCTGGGGGAGGATTGGTGCAGCCTGGGGCCT

CTCTGAGACTCTCCTGTGCAGCCTCTGGACGCACCTTCAGTAGTACAGG

CATGGGCTGGTTCCGACAGGCTCCAGGGAAGGAGCGTGAATTTGTAGCA

GCTATTAGCGGGGATGGTGATACTACATACTATGCAGACTCCGTGAAGG

GCCGATTCACCATCTCCAGAGACAACGCCAAGAACACGGTGTATCTGCA

AATGAACAGCCTGAAACCGTGGGACACGGCCGTTTATTACTGTGCTTCG

ACTCGGTTCACATGGGGCCTATATAGCGACTTTGTGAACTCCTATGAAT

ATGACGCCTGGGGCCAGGGGACCCCGGTCACCGTCTCCTCA;

-continued 3) nucleotide sequence of NBS1-10 (SEQ ID NO. 7):
CAGGTGCAGCTGGTGGAGTCTGGGGGAGGCTTGGTGCAACCTGGGGGT

CTCTGAGACTCTCCTGTGCAGCCTCTGGACGCACCTTCAGTAGTACAGG

CATGGGCTGGTTCCGACAGGGTCCAGGGAAGGAGCGTGAATTTGTAGCA

GCTATTAGCGGGGATGGTGATACTACATACTATGCAGACTCCGTGAAGG

GCCGATTCACCATCTCCAGAGACAACGCCAAGAACACGGTGTATCTGCA

AATGAACAGCCTGAAACCTGAGGACACGGCCGTTTATTACTGTGCTTCG

GCTCGGTTCACATGGGCCTATATAGCGACTTTGTGAACTCCTATGAAT

ATGACGCCTGGGGCCAGGGGACCCCGGTCACCGTCTCCTCA;
and 4) nucleotide sequence of NBS1-57 (SEQ ID NO. 8):
CAGGTGCAGCTCGTGGAGTCTGGGGGAGGATTGGTGCAGCCTGGGGCCT

CTCTGAGACTCTTTTGTGTAGCCTCTGGACGCACCTTCAGTAGTACAGG

CATGGGCTGGTTCCGACAGGCTCCAGGGAAGGAGCGTGAGTTTGTAGCA

GCTATTAGCGGTCCTGGTGATACTACATACTATGTCGACTCCGTGAAGG

GCCGATTCACCATCTCCAGAGACAACGCCAAGAACACGGTGTATCTGCA

AATGAACAGCCTGAAACCTGAGGACACGGCCGTTTATTACTGTGCTTCG

GCTGGGTTCACATGGGCCTATATAGCGACTTTGTGAACTCCTATGAAT

ATAACTACTGGGGCCAGGGGACCCCGGTCACCGTCTCCTCA.

Vector NTI software was used to analyze sequencing results, and the following framework regions (FR) and complementary determining regions (CDR) were determined. Functional area division was carried out on the four sequences as in Table 3 below:

Example 2 Affinity Detection Test of Nano Antibody for Neutralizing the Toxicity of SARS-CoV-2

1. Instrument and Reagent:

In this example, an instrument Gator® probe life was used to detect an intermolecular interaction with a thin film interference method. A sample to be detected with a concentration not less than 80% and an antigen RBD-FC protein (SARS-CoV-2 RBD protein) with a concentration not less than 90% were prepared.

Probe type: anti-human Fc antibody; and a kinetic index can be determined by the binding of anti-human Fc antibody and human Fc.

Buffer: Q buffer (PBS+0.02% Tween-20+0.2% BSA).

2. Experimental Method:
   1) Detection method of NBS1-2 sample: the nano antibody was detected with an immobilized antigen RBD-Fc (100 nM); the probe type used was the anti-human Fc antibody; and the NBS1-2 was diluted to 60,000 nM, 30,000 nM, 15,000 nM, 7,500 nM, 3,750 nM, 1,875 nM, 937.5 nM, and 0 nM with the Q buffer.
   2) Detection method of NBS1-3 sample: the nano antibody was detected with the immobilized antigen RBD-Fc (100 nM); the probe type used was the anti-human Fc antibody; and the NBS1-3 was diluted to 25 nM, 12.5 nM, 6.25 nM, 3.18 nM, 1.56 nM, 0.78 nM, and 0 nM with the Q buffer.
   3) Detection method of NBS1-10 sample: the nano antibody was detected with the immobilized antigen RBD-Fc (100 nM); the probe type used was the anti-human Fc antibody; and the NBS1-10 was diluted to 25 nM, 12.5 nM, 6.25 nM, 3.18 nM, 1.56 nM, 0.78 nM, and 0 nM with the Q buffer.

TABLE 3

| | Functional Area Division | | | |
|---|---|---|---|---|
| | NBS1-2 | NBS1-3 | NBS1-10 | NBS1-57 |
| CDR1 | GRTLSNYI (SEQ ID NO. 9) | GRTFSSTG (SEQ ID NO. 10) | SEQ ID NO. 10 | SEQ ID NO. 10 |
| CDR2 | ISRSGVIT (SEQ ID NO. 11) | ISGDGDTT (SEQ ID NO. 12) | SEQ ID NO. 12 | ISGPGDTT (SEQ ID NO. 13) |
| CDR3 | AASSSKYMATREYDY (SEQ ID NO. 14) | ASTRFTWGLYSDFVNSYEYDA (SEQ ID NO. 15) | ASARFTWGLYSDFVNSYEYDA (SEQ ID NO. 16) | ASAGFTWGLYSDFVNSYEYNY (SEQ ID NO. 17) |
| FR1 | QVQLVESGGGLVQAGDSLRLACAAT (SEQ ID NO. 18) | QVQLVESGGGLVQPGASLRLSCAAS (SEQ ID NO. 19) | QVQLVESGGGLVQPGGSLRLSCAAS (SEQ ID NO. 20) | QVQLVESGGGLVQPGASLRLFCVAS (SEQ ID NO. 21) |
| FR2 | MGWFRQAPGKEPLFVAA (SEQ ID NO. 22) | MGWFRQAPGKEREFVAA (SEQ ID NO. 23) | MGWFRQGPGKEREFVAA (SEQ ID NO. 24) | SEQ ID NO. 23 |
| FR3 | KYADSVEGRFTISRDNAKNTAYLQMTSLEPEDTAVYYC (SEQ ID NO. 25) | YYADSVKGRFTISRDNAKNTVYLQMNSLKPWDTAVYYC (SEQ ID NO. 26) | YYADSVKGRFTISRDNAKNTVYLQMNSLKPEDTAVYYC (SEQ ID NO. 27) | YYVDSVKGRFTISRDNAKNTVYLQMNSLKPEDTAVYYC (SEQ ID NO. 28) |
| FR4 | WGQGTQVTVSS (SEQ ID NO. 29) | SEQ ID NO. 29 | SEQ ID NO. 29 | SEQ ID NO. 29 |

4) Detection method of NBS1-57 sample: the nano antibody was detected with the immobilized antigen RBD-Fc (100 nM); the probe type used was the anti-human Fc antibody; and the NBS1-57 was diluted to 25 nM, 12.5 nM, 6.25 nM, 3.18 nM, 1.56 nM, 0.78 nM, and 0 nM with the Q buffer.

Figure 8:
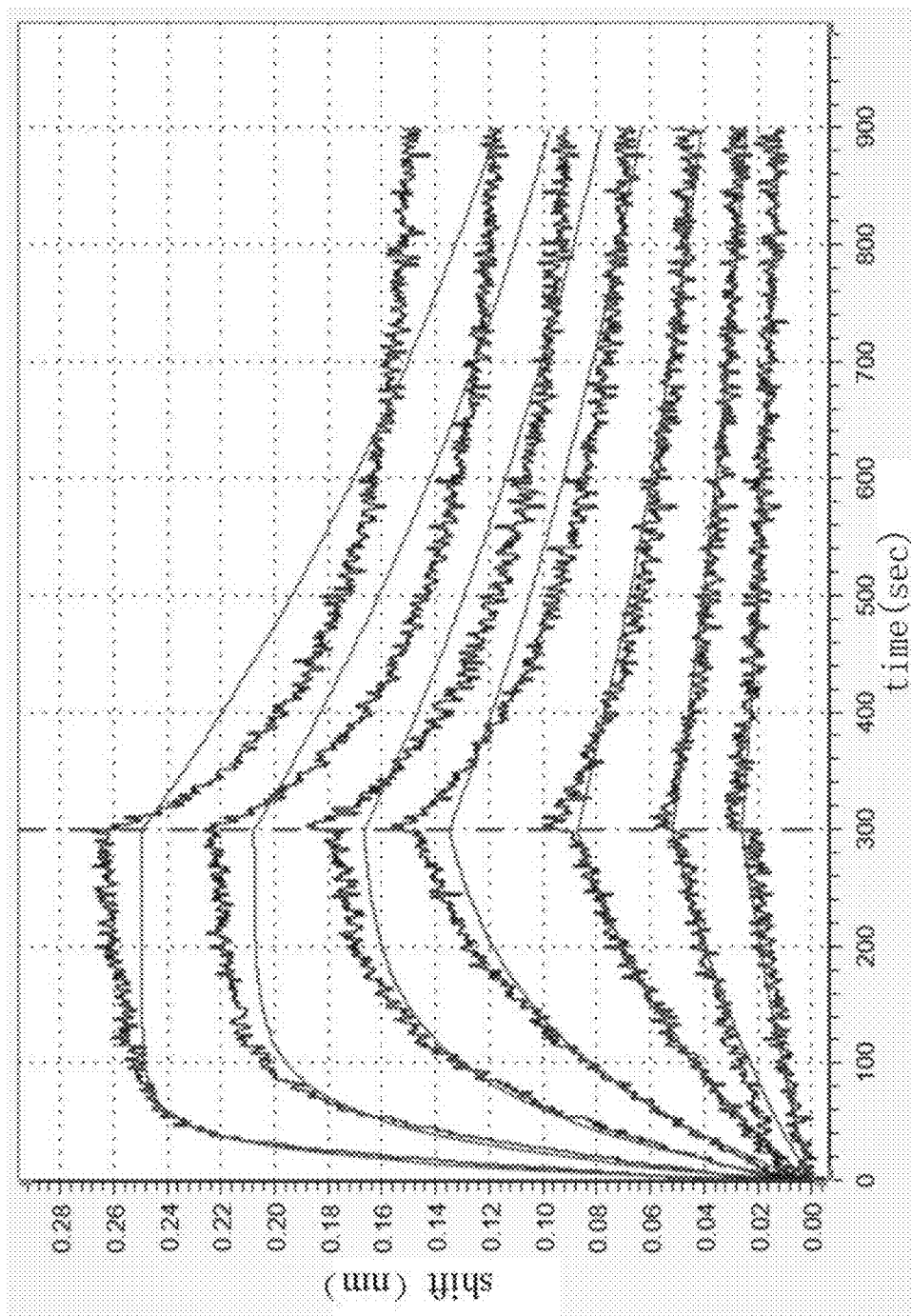
FIG. 8 is an affinity measurement diagram of NBS1-2 with RBD-Fc according to Example 2 of the present disclosure.
Figure 9:
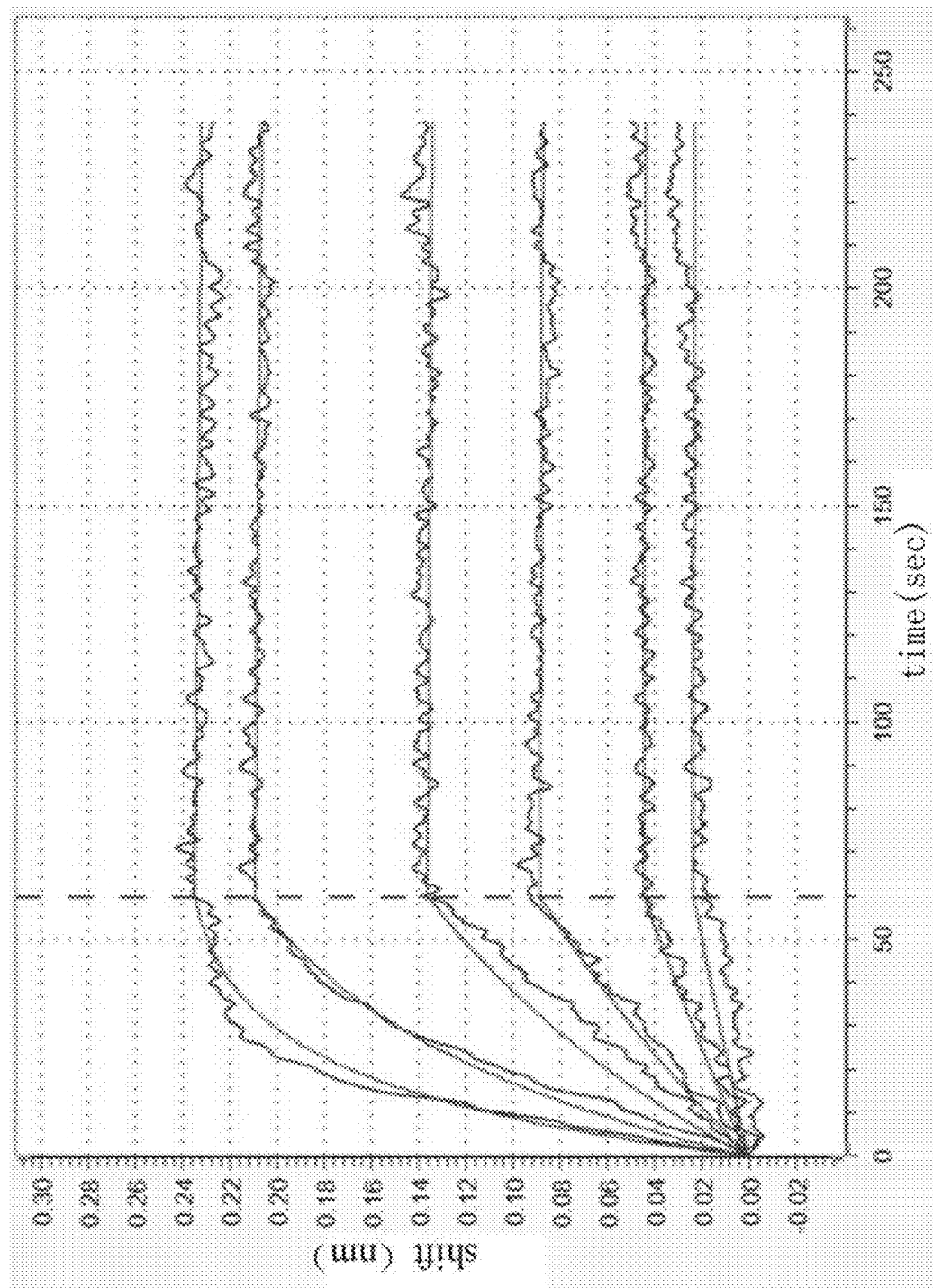
FIG. 9 is an affinity measurement diagram of NBS1-3 with the RBD-Fc according to Example 2 of the present disclosure.
Figure 10:
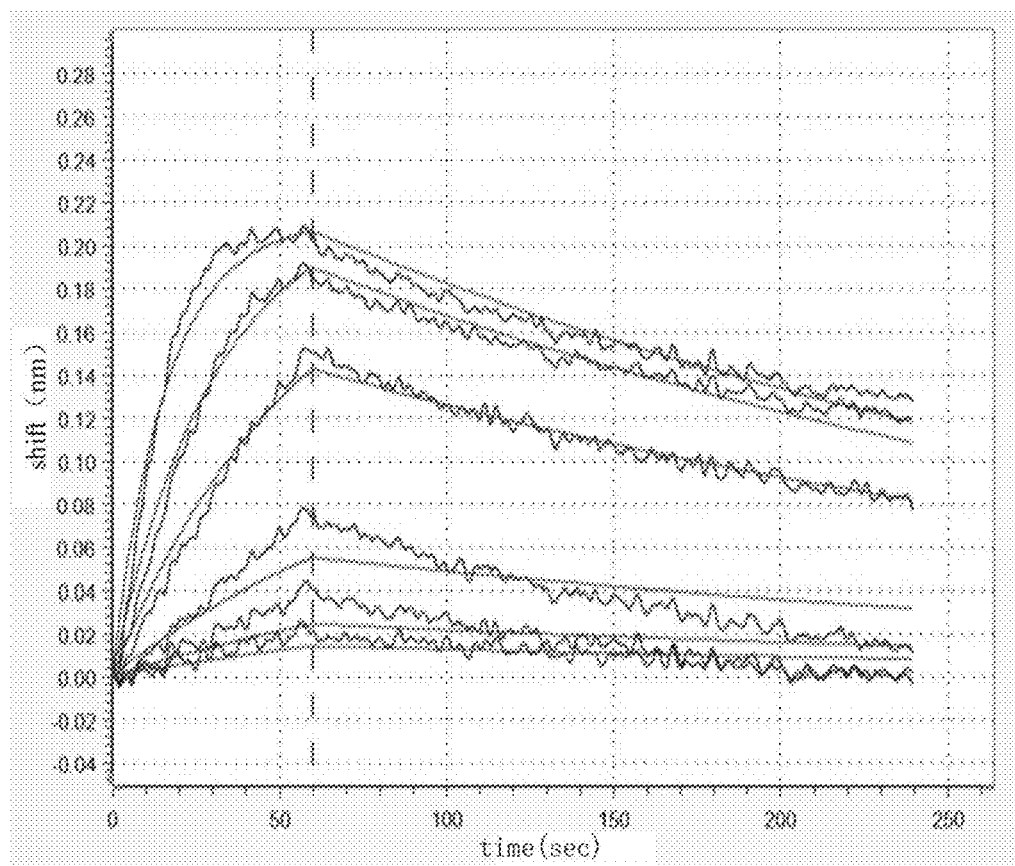
FIG. 10 is an affinity measurement diagram of NBS1-10 with the RBD-Fc according to Example 2 of the present disclosure.
Figure 11:
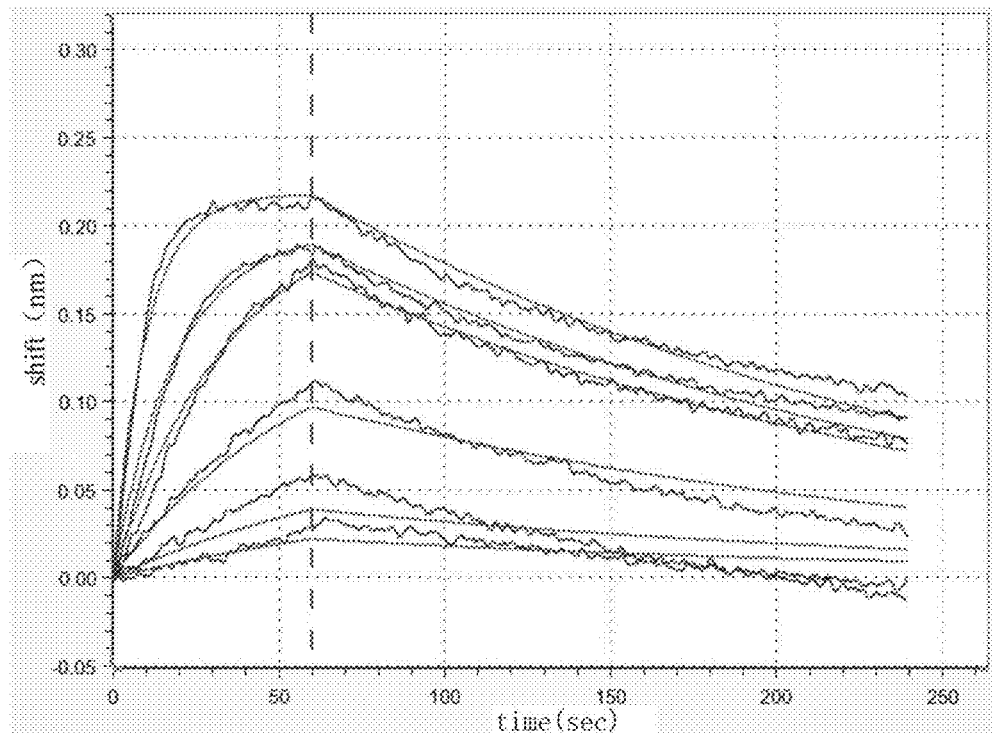
FIG. 11 is an affinity measurement diagram of NBS1-57 with the RBD-Fc according to Example 2 of the present disclosure.

3. Experimental Result and Analysis:

an antigen-antibody affinity was measured, and the affinity measurement diagrams are shown in FIG. 8 to FIG. 11 (wherein FIG. 8 is an affinity measurement diagram of NBS1-2-RBD-FC; FIG. 9 is an affinity measurement diagram of NBS1-3-RBD-Fc; FIG. 10 is an affinity measurement diagram of NBS1-10-RBD-Fc; and FIG. 11 is an affinity measurement diagram of NBS1-57-RBD-Fc). It can be seen that affinities of the several samples in the example of the present disclosure are shown in Table 4 below:

1. Experimental Method:

1) An original concentration of each protein sample was taken as an initial concentration. A gradient dilution with dilution concentrations of 1 mg/ml, 100 μg/ml, 10 μg/ml, 1 μg/ml, 0.1 μg/ml, and 0.01 μg/ml was carried out on each protein sample by using a sample diluent (20 mM PB, pH 7.2).

2) The diluted sample was incubated with a SARS-CoV-2 pseudovirus of an equal volume, and then used to infect cells to test an antiviral neutralization ability of the protein sample. A final detection concentration (actual detection concentration) of each sample is shown in Table 5 below.

TABLE 5

Final Detection Concentration of Sample

| | | Protein concentration (μg/ml) | | | | | |
|---|---|---|---|---|---|---|---|
| Protein number | Initial concentration | Concentration 1 | Concentration 2 | Concentration 3 | Concentration 4 | Concentration 5 | Concentration 6 |
| XBS1-2 | 1765 | 500 | 50 | 5 | 0.5 | 0.05 | 0.005 |
| NBS1-3 | 1720 | 500 | 50 | 5 | 0.5 | 0.05 | 0.005 |
| NBS1-10 | 470 | 470 | 50 | 5 | 0.5 | 005 | 0.005 |
| NBS1-57 | 480 | 480 | 50 | 5 | 0.5 | 0.05 | 0.005 |

Note: the diluted protein sample needed to be incubated with the pseudovirus of the equal volume, so that the final concentration of the sample was ½ of the initial diluted concentration of the sample.

TABLE 4

Affinity Test of Nano Antibody

| Sample name | koff (1/s) | kon (1/Ms) | $K_D$ (M) |
|---|---|---|---|
| NBS1-3 | $7.16 \times 10^{-5}$ | $2.38 \times 10^{6}$ | $3.01 \times 10^{-11}$ |
| NBS1-57 | $4.91 \times 10^{-3}$ | $3.80 \times 10^{6}$ | $1.29 \times 10^{-9}$ |
| NBS1-10 | $3.11 \times 10^{-3}$ | $2.37 \times 10^{6}$ | $1.31 \times 10^{-9}$ |
| NBS1-2 | $1.27 \times 10^{-3}$ | $8.95 \times 10^{2}$ | $1.41 \times 10^{-6}$ |

Wherein, koff refers to a dissociation rate constant, kon refers to a binding rate constant, and $K_D$ ($K_D$=koff/kon) refers to an equilibrium dissociation constant, which are used to characterize the affinity of the nano antibody to the RBD-Fc protein. If $K_D$ value is larger, the drug concentration needed to cause a maximum effect is larger, and the affinity is lower. It can be seen from the results that the four nano antibody samples all have a high affinity with the antigen RBD-Fc protein, wherein the sample NBS1-3 has the highest affinity, so that it can be inferred that a potential neutralizing effect thereof on the SARS-CoV-2 is the best.

Example 3 Virus Neutralization Test of Nano Antibody for Neutralizing the Toxicity of SARS-CoV-2

Virus neutralization test is a technique used to detect specific antibodies. It uses known viruses to determine the biological activity interference ability of the tested antibody. In the examples of the present invention, this technology was used to detect an activity of a screened nano antibody.

Four nano antibody samples with a purity larger than 80%: NBS1-2, NBS1-3, NBS1-10, and NBS 1-57 were prepared. The used nano antibodies were prepared in Example 1.

The virus concentration used in the present disclosure was 500TCID50, wherein TCID50 referred to an infection amount of half cell cultures and was a calculated index. A calculation method of the TCID50 used in the present disclosure was the Reed-Muench method (the TCID50 has two calculation methods: the Reed-Muench method or the Karber method).

2. Experimental Result:

50% inhibition concentration ($IC_{50}$) and 90% inhibition concentration ($IC_{90}$) against the SARS-CoV-2 pseudovirus of each sample can be seen from Table 5. A neutralization titer is obtained through probit regression analysis by SPSS software.

Figure 12:
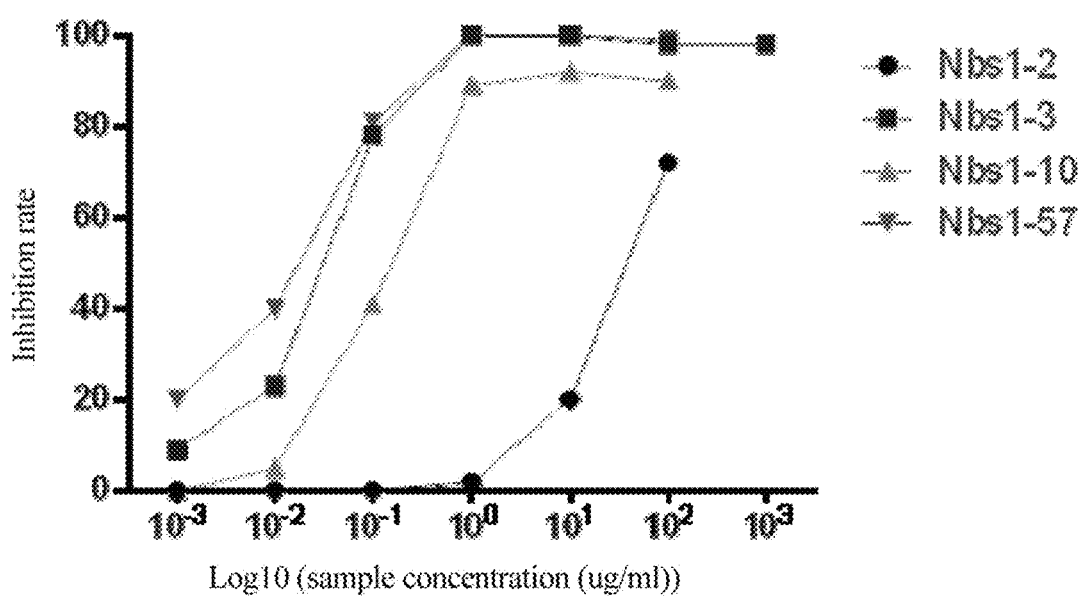
FIG. 12 shows inhibition rates of samples with different concentrations for SARS-CoV-2 according to Example 3 of the present disclosure.

FIG. 12 shows the neutralizing ability of the protein sample to the SARS-CoV-2 pseudovirus at different concentrations. An x-coordinate is a protein concentration, and a y-coordinate is a neutralization inhibition level percentage. Each point represents a mean±SEM of three repeated wells under each experimental condition.

It can be seen from the test results in FIG. 12 that four nano antibody samples in the example of the present disclosure have a strong inhibition ability against the virus at a high concentration, wherein the NBS1-3 and the NBS1-57 can reach nearly 100% inhibition rate at a concentration of 1 μg/ml, and can also reach a high inhibition rate of 80% at a concentration of 0.1 μg/ml; the NBS1-10 also has a high inhibition rate close to 90% at a concentration of 1 μg/ml; the NBS1-2 has a relatively low inhibition rate, which can also reach 70% at a concentration of 100 μg/ml.

Therefore, the following conclusions can be drawn through the analysis of FIG. 12.

1) The four nano antibodies prepared by the present disclosure have an inhibition ability to virus infection at a high concentration.

2) The NBS1-3 and the NBS1-57 have a strong antiviral effect.
3) The NBS1-2 shows a relatively weak neutralizing ability to the SARS-CoV-2 pseudovirus.

The four nano antibody samples in the example of the present disclosure have a strong inhibition ability to the virus at a high concentration, i.e., an inhibition rate as high as 100% at the concentration of 1 µg/ml, show a strong neutralization ability to the SARS-CoV-2 pseudovirus, have a strong antiviral effect, and can be used for treating COVID-19.

The above mentioned are the only examples of the present disclosure, which do not limit the protection scope of the present disclosure. Any equivalent transformation made by the contents of the specification and the drawings of the present disclosure, or directly or indirectly applied in a related technical field, is similarly included in the protection scope of the present disclosure.

What is claimed is:

1. An antibody for inhibiting SARS-CoV-2 infection, comprising a complementarity determining region CDR, wherein the complementarity determining region CDR comprises a CDR1, a CDR2 and a CDR3;
 the amino acid sequence of the CDR1 is SEQ ID NO: 10;
 the amino acid sequence of the CDR2 is SEQ ID NO: 12; and
 the amino acid sequence of the CDR3 is SEQ ID NO: 15.

2. The antibody for inhibiting SARS-CoV-2 infection according to claim 1, further comprising a framework region FR, wherein the framework region FR comprises a FR1, a FR2, a FR3 and a FR4;
 the amino acid sequence of the FR1 is SEQ ID NO: 19;
 the amino acid sequence of the FR2 is SEQ ID NO: 23;
 the amino acid sequence of the FR3 is SEQ ID NO: 26; and
 the amino acid sequence of the FR4 is SEQ ID NO: 29.

3. The antibody for inhibiting SARS-CoV-2 infection according to claim 1, wherein the amino acid sequence of the antibody is SEQ ID NO: 2.

4. A preparation method of the antibody for inhibiting SARS-CoV-2 infection according to claim 1, comprising the following steps of:
 (1) cloning the nucleotide sequence SEQ ID NO: 6 into an expression vector to obtain a recombinant plasmid, and transferring the recombinant plasmid into a host cell to induce expression of the antibody; and
 (2) purifying the antibody from the host cell.

5. A gene encoding an antibody for inhibiting SARS-CoV-2 infection, wherein the nucleotide sequence of the gene is SEQ ID NO: 6.

6. A recombinant plasmid, comprising the nucleotide sequence SEQ ID NO: 6.

7. A recombinant cell, comprising the nucleotide sequence SEQ ID NO: 6.

* * * * *